United States Patent
Monda et al.

(10) Patent No.: US 11,083,678 B2
(45) Date of Patent: Aug. 10, 2021

(54) HAIR DYEING METHOD

(71) Applicant: KAO CORPORATION, Tokyo (JP)

(72) Inventors: Keiji Monda, Katsusika-ku (JP); Takeshi Iizaki, Saitama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/648,975

(22) PCT Filed: Sep. 20, 2018

(86) PCT No.: PCT/JP2018/034758
§ 371 (c)(1),
(2) Date: Mar. 19, 2020

(87) PCT Pub. No.: WO2019/059263
PCT Pub. Date: Mar. 28, 2019

(65) Prior Publication Data
US 2020/0289389 A1    Sep. 17, 2020

(30) Foreign Application Priority Data

Sep. 20, 2017 (JP) .............. JP2017-180753
Feb. 28, 2018 (JP) .............. JP2018-035694

(51) Int. Cl.
*A61Q 5/10* (2006.01)
*A61K 8/49* (2006.01)
*A61K 8/34* (2006.01)

(52) U.S. Cl.
CPC ............ *A61K 8/49* (2013.01); *A61K 8/34* (2013.01); *A61K 8/345* (2013.01); *A61K 8/494* (2013.01);
(Continued)

(58) Field of Classification Search
CPC .......... A61Q 5/10; A61Q 5/065; A61K 8/494; A61K 8/49; A61K 2800/4324;
(Continued)

(56) References Cited

U.S. PATENT DOCUMENTS

2004/0019982 A1   2/2004   Pratt et al.
2010/0154135 A1   6/2010   Matsunaga et al.
(Continued)

FOREIGN PATENT DOCUMENTS

EP   2 151 232 A1   2/2010
EP   2 883 530 A1   6/2015
(Continued)

OTHER PUBLICATIONS

STIC Search Report dated Aug. 28, 2020.*
International Search Report dated Dec. 13, 2018 in PCT/JP2018/034758 filed Sep. 20, 2018.

*Primary Examiner* — Eisa B Elhilo
(74) *Attorney, Agent, or Firm* — Oblon, McClelland, Maier & Neustadt, L.L.P.

(57) ABSTRACT

A hair dyeing method including the following steps (I) and (II): step (I): mixing a first agent comprising an alkaline agent and an oxidation dye precursor, a second agent comprising an oxidizing agent, and a third agent comprising one or more dyes (A) selected from the group consisting of the following (A-1), (A-2), and (A-3), having a pH at 25° C. of 7.5 or more and 12 or less when diluted to be 10 times by mass with water; and step (II): applying a mixed solution prepared in step (I) on hair.

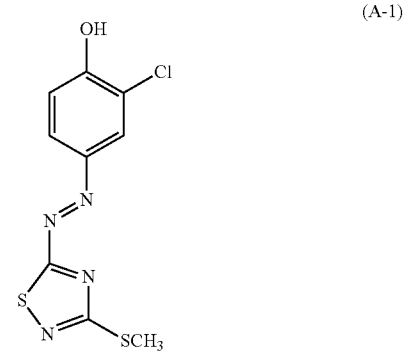

(A-1)

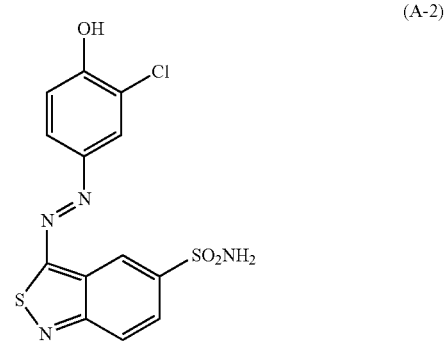

(A-2)

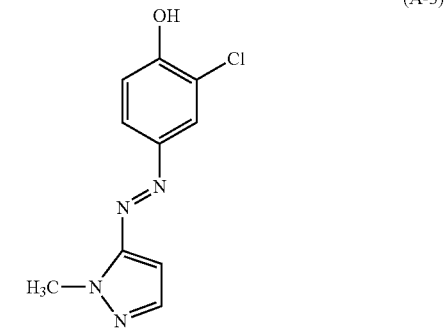

(A-3)

12 Claims, No Drawings

(52) U.S. Cl.
CPC ........ *A61Q 5/10* (2013.01); *A61K 2800/4324* (2013.01); *A61K 2800/882* (2013.01)

(58) Field of Classification Search
CPC .... A61K 2800/882; A61K 8/34; A61K 8/345; A61K 8/46; A61K 2800/432
USPC .......................................................... 8/405
See application file for complete search history.

(56) References Cited

U.S. PATENT DOCUMENTS

| | | |
|---|---|---|
| 2012/0017931 A1 | 1/2012 | Frohling |
| 2017/0196791 A1 | 7/2017 | Nojiri |
| 2017/0258695 A1 | 9/2017 | Consoli et al. |
| 2018/0340107 A1 | 11/2018 | Noecker et al. |

FOREIGN PATENT DOCUMENTS

| | | | | |
|---|---|---|---|---|
| EP | 2883530 A1 * | 6/2015 | ............... | A61Q 5/10 |
| EP | 3 153 154 A1 | 4/2017 | | |
| JP | 6-271435 A | 9/1994 | | |
| JP | 2003-342139 A | 12/2003 | | |
| JP | 2010-24158 A | 2/2010 | | |
| JP | 2019-55944 A | 4/2019 | | |
| JP | 2019-55945 A | 4/2019 | | |
| JP | 2019-55946 A | 4/2019 | | |
| JP | 2019-55947 A | 4/2019 | | |
| JP | 2019-151616 A | 9/2019 | | |
| WO | WO 2017/041907 A1 | 3/2014 | | |

* cited by examiner

HAIR DYEING METHOD

TECHNICAL FIELD

The present invention relates to a hair dyeing method.

BACKGROUND ART

A hair dye agent can be classified by dyes to be used, or the presence or absence of the action of bleaching on melanin. Typical examples thereof may include a two-agent type permanent hair dye agent containing a first agent containing an alkaline agent and an oxidation dye intermediate, a second agent containing an oxidizing agent, or a one-agent type semi-permanent hair dye agent including an organic acid or alkaline agent, and at least one direct dye such as an acidic dye, a basic dye and a nitro dye.

The permanent hair dye agent has an excellent aspect that the dye agent penetrates into a deep portion of hair, and uniformly dyes hair from the core to the surface, so that the dyed color hardly fades, and the hair dyeing effect lasts long, whereas the hair dye agent has a problem that the color tone imparted by the oxidation dye is not very vivid. In addition, the direct dyes include dyes which can produce vivid colors such as a nitro dye (e.g., see PTL 1), but has a problem that fading of the dyed hair becomes significant with the lapse of time. Thus, a method of using the direct dye in combination with the oxidation dye to give a more vivid color, in the permanent hair dye agent has been proposed (e.g., see PTL 2).

(PTL 1) JP Hei 6-271435 A
(PTL 2) JP 2010-024158 A

SUMMARY OF INVENTION

The present invention provides a hair dyeing method including the following steps (I) and (II):

step (I): mixing a first agent comprising an alkaline agent and an oxidation dye precursor, a second agent comprising an oxidizing agent, and a third agent comprising one or more dyes (A) selected from the group consisting of the following (A-1), (A-2), and (A-3), having a pH at 25° C. of 7.5 or more and 12 or less when diluted to be 10 times by mass with water; and step (II): applying a mixed solution prepared in step (I) on hair.

[Chem. 1]

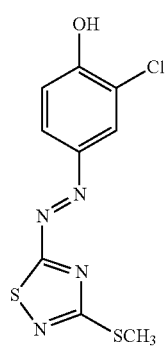

(A-1)

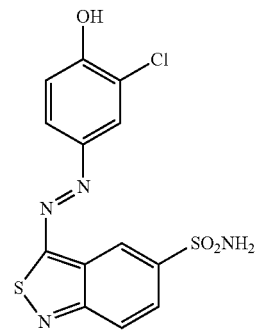

(A-2)

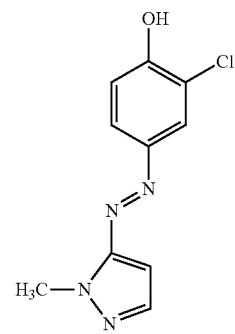

(A-3)

DETAILED DESCRIPTION OF THE INVENTION

There are few direct dyes which are stable to an alkaline agent or an oxidizing agent, and so it is difficult to exert the effect of the direct dye on the permanent hair dye agent. Therefore, applying the effective amounts of the oxidation dye precursor and the direct dye to hair at the same time has currently not been achieved.

Meanwhile, from understanding that the hair color is very vivid when a certain azo dye is used to perform dyeing, the present inventors examined a hair dyeing method by using a certain azo dye in combination with an oxidation dye precursor to gain benefit from both dyes. As a result, it was found that when the azo dye permeates into a certain portion of hair, the hair can be dyed in two layers of colors, and the hue or color tone of hair appearance is changed depending on the viewing angle to the hair, which is an unprecedented effect.

Accordingly, the present invention relates to a hair dyeing method in which an oxidation dye precursor and an azo dye are used in combination to sufficiently exert the properties of both dyes, so that hair is dyed in two layers of colors, thereby obtaining a hair dyeing effect to change the hue or color tone of hair appearance depending on the viewing angle to the hair.

The present inventors have found that when a certain azo dye is used in combination with an oxidation dye precursor in a permanent hair dye agent, the azo dye is contained in a composition other than a first agent and a second agent, and then mixed with the first agent and the second agent immediately before use, and applied on hair, thereby appropriately obtaining a dyeing effect to change the hue or color tone of hair appearance depending on the viewing angle to the hair, just by application of one mixture on hair.

The present invention provides a dyeing effect to change the hue or color tone of hair appearance depending on the viewing angle to the hair, the oxidation dye precursor and the azo dye are used in combination, and hair is dyed in two layers of colors at one time.

The first agent used in step (I) of the present invention contains an alkaline agent and an oxidation dye precursor.

(Alkaline Agent)

The alkaline agent contained in the first agent may include for example, ammonia and the salts thereof, alkanolamine such as sodium hydroxide, potassium hydroxide, monoethanolamine, isopropanolamine, 2-amino-2-methylpropanol and 2-aminobutanol, and the salts thereof, alkanediamine such as 1,3-propanediamine and the salts thereof, and carbonates such as sodium carbonate, potassium carbonate, sodium hydrogen carbonate, potassium hydrogen carbonate and guanidine carbonate. Among the alkaline agent, ammonia, alkanol amine, and the salts thereof are preferable. As the ammonium salt, ammonium carbonate and ammonium hydrogen carbonate are preferable, and as the alkanol amine and the salts thereof, monoethanolamine and the salt thereof are preferable.

The alkaline agent may be used alone or in combination of two or more. The content of the alkaline agent in the first agent is preferably 0.1% by mass or more, more preferably 0.2% by mass or more, further more preferably 0.4% by mass or more, and further more preferably 0.8% by mass or more, from the viewpoint of sufficiently swelling hair to obtain the hair dyeing effect, and preferably 14% by mass or less, more preferably 12% by mass or less, further more preferably 8% by mass or less, and further more preferably 6% by mass or less, from the viewpoint of suppressing hair damage or skin irritation.

(Oxidation Dye Precursor)

As the oxidation dye precursor contained in the first agent, a general precursor used in a hair dye agent can be used.

The precursor may include for example, p-phenylenediamine, toluene-2,5-diamine, o-chloro-p-phenylenediamine, N-phenyl-p-phenylenediamine, N,N-bis(hydroxyethyl)-p-phenylenediamine, 3-methyl-4-aminophenol, 2-hydroxyethyl-p-phenylenediamine, p-aminophenol, p-methylaminophenol, 4-amino-m-cresol, o-aminophenol, 2-methoxymethyl-p-phenylenediamine, hydroxyethoxyaminopyrazolopyridine, 2,3-diaminodihydroxypyrazolopyrazolone, N-methoxyethyl-p-phenylenediamine, 2,6-dimethyl-p-phenylenediamine, 4,4'-diaminodiphenylamine, 1,3-bis(N-(2-hydroxyethyl)-N-(4-aminophenyl)amino)-2-propanol, PEG-3,2,2'-p-phenylenediamine, 2-aminomethyl-4-aminophenol, 2-(2-hydroxyethyl aminomethyl)-4-aminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine, 4,5-diamino-1-(4'-chlorobenzyl)pyrazole, and salts thereof.

The precursor may be used alone or in combination of two or more. The content of the precursor in the first agent is preferably 0.003% by mass or more, more preferably 0.005% by mass or more, further more preferably 0.01% by mass or more, and further more preferably 0.05% by mass or more, from the viewpoint of obtaining a sufficient hair dyeability, and preferably 10% by mass or less, more preferably 8% by mass or less, further more preferably 5% by mass or less, and further more preferably 3% by mass or less, from the viewpoint of stability of the agent.

The first agent may contain a coupler, and the coupler may include for example, resorcin, 2-methyl resorcin, 1-naphthol, 1,5-dihydroxynaphthalene, 5-amino-o-cresol, m-phenylenediamine, m-aminophenol, 2,4-diaminophenoxyethanol, 2,6-diaminopyridine, 2-methyl-5-hydroxyethylaminophenol, 2-amino-3-hydroxypyridine, p-aminophenol, o-aminophenol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, 2-methyl-5-aminophenol, 2,4-dichloro-3-aminophenol, 2-chloro-3-amino-6-methylphenol, 2-methyl-4-chloro-5-aminophenol, N-cyclopentyl-m-aminophenol, 2-methyl-4-methoxy-5-(2-hydroxyethylamino)phenol, 2-methyl-4-fluoro-5-aminophenol, 4-chlororesorcin, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, and salts thereof.

The coupler may be used alone or in combination of two or more. The content of the coupler in the first agent is preferably 0.003% by mass or more, more preferably 0.005% by mass or more, further more preferably 0.01% by mass or more, and further more preferably 0.05% by mass or more, from the viewpoint of obtaining a sufficient hair dyeability, and preferably 10% by mass or less, more preferably 8% by mass or less, further more preferably 5% by mass or less, and further more preferably 3% by mass or less, from the viewpoint of stability of the agent.

The second agent used in step (I) of the present invention includes an oxidizing agent.

(Oxidizing Agent)

The oxidizing agent contained in the second agent may include for example, hydrogen peroxide; persulfates such as ammonium persulfate, potassium persulfate and sodium persulfate; perborates such as sodium perborate; percarbonates such as sodium percarbonate; bromates such as sodium bromate and potassium bromate. Among them, hydrogen peroxide is particularly preferable, in the viewpoint of hair bleachability, stability of a dye, and effectiveness of a dye.

The oxidizing agent may be used alone or in combination of two or more. The content of the oxidizing agent in the second agent is preferably 0.5% by mass or more, more preferably 1% by mass or more, further more preferably 2% by mass or more, further more preferably 3% by mass or more, from the viewpoint of hair bleachability and a hair dyeability, and preferably 20% by mass or less, more preferably 15% by mass or less, further more preferably 13% by mass or less, further more preferably 10% by mass or less, further more preferably 6.5% by mass, from the viewpoint of suppressing skin irritation or hair damage.

The third agent used in step (I) of the present invention contains the following dye (A).

(Dye (A))

The third agent contains one or more dyes (A) selected from the group consisting of the following (A-1), (A-2), and (A-3). Dye (A) is an azo dye, and relatively stable to the alkaline agent, as compared with a general direct dye, however, when dye (A) is contained in the first agent, there is a possibility that the effective amount is decreased over time by storage. However, in the present invention, component (A) is contained in the third agent which is different from the first and second agents, and mixed immediately before use and applied to hair, and thus, there is no need to concern a decrease of the effective amount of component (A), and the dyeing effect to change the hue or color tone depending on the viewing angle can be sufficiently obtained.

[Chem. 2]

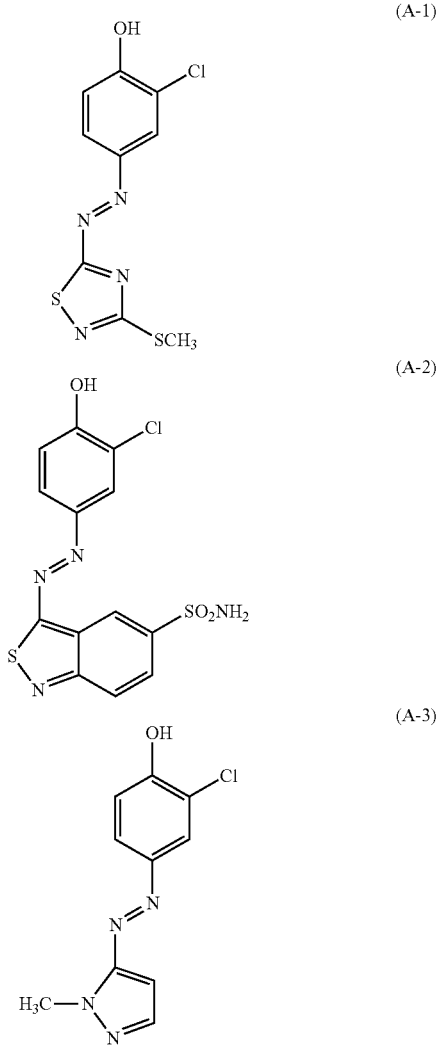

The pKa of azo dyes (A-1), (A-2), and (A-3) is 6.0, 6.0 and 7.5, respectively, and as the protons are dissociated, (A-1) represents red, (A-2) represents blue, and (A-3) represents yellow.

The content of dye (A) in the third agent is preferably 0.2% by mass or more, more preferably 0.5% by mass or more, further more preferably 0.8% by mass or more, further more preferably 1% by mass or more, from the viewpoint of obtaining the sufficient hair dyeability, and changing the hue or color tone of hair appearance depending on the viewing angle to the hair, and preferably 50% by mass or less, more preferably 20% by mass or less, further more preferably 10% by mass or less, further more preferably 5% by mass or less, from the viewpoint of storage stability.

In the third agent, the alkaline agent may be contained. As the alkaline agent to be contained, those described for the first agent may be used, however, as the alkaline agent to be contained in the third agent, alkanol amine and the salt thereof are preferable, monoethanolamine and 2-amino-2-methylpropanol are more preferable, and among them, 2-amino-2-methylpropanol is preferable, from the viewpoint of changing the hue or color tone of hair appearance depending on the viewing angle to the hair. These alkaline agents may be used alone or in combination of two or more.

In addition, in the third agent or the first agent, the direct dye other than dye (A) may be further contained. However, from the viewpoint of not affecting dyeability by dye (A), it is preferable that a ratio of dye (A) in the entire dye in a mixed solution of the first to third agents (hereinafter, simply referred to as a "mixed solution") be 1% by mass or more and 100% by mass or less, furthermore 5% by mass or more 100% by mass or less, furthermore 10% by mass or more and 100% by mass or less, and furthermore 20% by mass or more and 100% by mass or less.

The direct dye other than dye (A) may include anionic dyes, cationic dyes, and neutral dyes. The anionic dye may include, for example, Acid Black 1, Acid Blue 1, Acid Blue 3, Food Blue No. 2, Food Blue No. 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, Acid Orange 24, Acid Green 25, Solvent Green 7, Solvent Red 73, Acid Red 95, Solvent Red 43, Solvent Red 48, Acid Red 33, Solvent Violet 13, Acid Yellow 73, Food Red No. 17, Food Red No. 1, Food Yellow No. 3, Food Blue No. 2, Food Black No. 1, Food Black No. 2, Disperse Black 9, Disperse Violet 1, and the alkali metal salts thereof (sodium salt or potassium salt). The cationic dye may include for example, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12, Basic Red 22, Basic Red 76, Basic Violet 1, Basic Violet 2, Basic Violet 3, Basic Violet 10, Basic Violet 14, Basic Yellow 57, Basic Red 51, Basic Yellow 87, Basic Blue 17, and Basic Yellow 31. The neutral dye including a nitro dye may include for example, HC Blue 2, HC Blue 4, HC Blue 5, HC Blue 6, HC Blue 7, HC Blue 8, HC Blue 9, HC Blue 10, HC Blue 11, HC Blue 12, HC Blue 13, HC Brown 1, HC Brown 2, HC Green 1, HC Orange 1, HC Orange 2, HC Orange 3, HC Orange 5, HC Red BN, HC Red 1, HC Red 3, HC Red 7, HC Red 8, HC Red 9, HC Red 10, HC Red 11, HC Red 13, HC Red 54, HC Red 14, HC Violet BS, HC Violet 1, HC Violet 2, HC Yellow 2, HC Yellow 4, HC Yellow 5, HC Yellow 6, HC Yellow 7, HC Yellow 8, HC Yellow 9, HC Yellow 10, HC Yellow 11, HC Yellow 12, HC Yellow 13, HC Yellow 14, HC Yellow 15, 2-amino-6-chloro-4-nitrophenol, picramic acid, 1,2-diamino-4-nitrobenzene, 1,4-diamino-2-nitrobenzene, 3-nitro-4-aminophenol, 1-hydroxy-2-amino-3-nitrobenzene, 2-hydroxyethyl picramic acid, 3-nitro-p-hydroxyethylaminophenol, and 4-hydroxypropylamino-3-nitrophenol N,N-bis(2-hydroxyethyl)-2'-nitro-p-phenylenediamine.

(Surfactant)

The first to third agents used in step (I) of the present invention may contain a surfactant, from the viewpoint of hair touch feel and emulsification performance. As the surfactant, any one of a cationic surfactant, a nonionic surfactant, an amphoteric surfactant, and an anionic surfactant may be used.

The cationic surfactant may be preferably mono long-chain alkyl quaternary ammonium salts, and may include preferably for example, cetrimonium chloride, steartrimonium chloride, behentrimonium chloride, stearalkonium chloride, and benzalkonium chloride.

The nonionic surfactant may include for example, polyoxyalkylene alkyl ether, polyoxyalkylene alkenyl ether, higher fatty acid sucrose ester, polyglycerin fatty acid ester, higher mono- or di-ethanolamide, polyoxyethylene hydrogenated castor oil, polyoxyethylene sorbitan fatty acid ester, polyoxyethylene sorbit fatty acid ester, alkyl saccharide, alkylamine oxide, and alkylamidoamine oxide.

The amphoteric surfactant may include for example, imidazoline, carbobetaine, amidobetaine, sulfobetaine, hydroxysulfobetaine, and amidosulfobetaine.

The anionic surfactant may include for example, alkylbenzene sulfonate, alkyl or alkenyl ether sulfate, alkyl or alkenyl sulfate, olefin sulfonate, alkane sulfonate, saturated or unsaturated fatty acid salt, alkyl or alkenyl ether carboxylate, α-sulfo fatty acid salt, N-acyl amino acid, phosphoric acid mono- or di-ester, and sulfosuccinic acid ester. The alkyl ether sulfate may include polyoxyethylene alkyl ether sulfate. The counter ion of the anionic group of these anionic surfactants may include alkali metal ions such as sodium ion and potassium ion; alkali earth metal ions such as calcium ion and magnesium ion; ammonium ion; and alkanol amine having one to three alkanol groups having 2 or 3 carbon atoms (e.g., monoethanolamine, diethanolamine, triethanolamine, and triisopropanolamine).

These surfactants may be used alone or in combination of two or more. The content of the surfactant in the mixed solution is preferably 0.1% by mass or more, more preferably 0.2% by mass or more, and further more preferably 0.5% by mass or more, and preferably 30% by mass or less, more preferably 20% by mass or less, and further more preferably 15% by mass or less, from the viewpoint of hair touch feel and emulsification performance.

(Thickening Agent)

The first to third agents used in step (I) of the present invention may further contain a synthetic polymeric compound, a semisynthetic polymeric compound, or natural polymeric compound as a thickening agent, from the viewpoint of applying the mixed solution on hair uniformly, and adjusting the viscosity of the agent so that the agent does not drip down while it stands. The synthetic polymeric compound, the semisynthetic polymeric compound, and the natural polymeric compound may include for example, a (vinyl pyrrolidone/methacrylic acid dimethyl aminoethyl) copolymer (e.g., Copolymer 845, Copolymer 937, Copolymer 958; ISP Japan), methyl cellulose (e.g., METOLOSE SM; Shin-Etsu Chemical Co., Ltd.), ethyl cellulose (e.g., EMULFREE CBG; Ikeda Corporation), hydroxyethyl cellulose (e.g., CELLOSIZE QP4400H, QP52000H; Dow Chemical Japan limited, SE-600, SE-850; Daicel Corporation), hydroxy propyl cellulose (e.g., NISSO HPC-H, HPC-M; Nippon Soda, Co., Ltd.), hydroxypropyl xanthan gum (e.g., Raporugamu EX; Sumitomo Dainippon Pharma Co., Ltd.), Pullulan (e.g., Pullulan PF-20, Pullulan PI-20; Hayashibara Co., Ltd.), and Xanthan Gum (e.g., Eco-Gum; Sumitomo Dainippon Pharma Co., Ltd.).

These thickening agents may be used alone or in combination of two or more. The content of the thickening agent in the mixed solution is preferably 0.05% by mass or more, more preferably 0.1% by mass or more, further more preferably 0.5% by mass or more, and preferably 20% by mass or less, more preferably 10% by mass or less, further more preferably 5% by mass or less, from the viewpoint of applying the mixed solution on hair uniformly, and adjusting the viscosity of the agent so that the mixed solution does not drip down while it stands.

(Conditioning Component)

The first to third agents to be used in step (I) of the present invention may contain a conditioning component appropriate for application to hair, and the conditioning component is generally a polymer or oil which is soluble or dispersible in the liquid hair dye composition, and adhered on hair when rinsing or diluted with water or shampoo. The conditioning component may include a cationic polymer, silicone, a higher alcohol, and an organic conditioning oil.

Cationic Polymer

The cationic polymer refers to a polymer having a cationic group or a group which can be ionized to a cationic group, and includes an amphoteric polymer which becomes cationic as a whole. That is, the cationic polymer may include for example, a polymer including an amino group or an ammonium group in the side chain of the polymer chain, or a diaryl quaternary ammonium salt as a structural unit, for example, cationized cellulose, cationic starch, cationized guar gum, a polymer or copolymer of diaryl quaternary ammonium salt, and quaternized polyvinyl pyrrolidone. Among them, a polymer containing diaryl quaternary ammonium salt as a structural unit, quaternized polyvinyl pyrrolidone, and cationized cellulose are preferable, and a polymer or copolymer of diaryl quaternary ammonium salt, and cationized cellulose are more preferable, from the viewpoint of effects of softness, smoothness, and ease of running fingers through hair during shampooing, ease of arrangement during drying, and moisture retention, and storage stability of the composition.

Specific examples of the cationic polymer may include for example, a dimethyldiarylammonium chloride polymer (polyquaternium-6, for example, Merquat 100; Nalco Japan Co., Ltd.), a dimethyldiarylammonium chloride/acrylic acid copolymer (polyquaternium-22, for example, Merquat 280, Merquat 295; Nalco Japan Co., Ltd.), a dimethyldiarylammonium chloride/acrylamide copolymer (polyquaternium-7, for example, Merquat 550; Nalco Japan Co., Ltd.), quaternized polyvinyl pyrrolidone (polyquaternium-11, for example, GAFQUAT 734, GAFQUAT 755, GAFQUAT 755N; ISP Japan), cationized cellulose (polyquaternium-10, for example, LEOGARD G, LEOGARD GP; LION CORPORATION, Polymer JR-125, Polymer JR-400, Polymer JR-30M, Polymer LR-400, Polymer LR-30M; Dow chemical Japan limited), and a hydroxyethyl cellulose/dimethyldiarylammonium chloride copolymer (polyquaternium-4, for example, CELQUAT H-100, CELQUAT L-200 (National Starch and Chemical Company)).

These cationic polymers may be used alone or in combination of two or more, and the content of the cationic polymer in the liquid hair dye composition is preferably 0.001% by mass or more, more preferably 0.01% by mass or more, and further more preferably 0.05% by mass or more, and preferably 20% by mass or less, more preferably 10% by mass or less, and further more preferably 5% by mass or less, from the viewpoint of improving hair touch feel and the storage stability of the composition.

Silicone

The silicone may include for example, dimethyl polysiloxane, modified silicone (e.g., amino-modified silicone, fluorine-modified silicone, alcohol-modified silicone, polyether-modified silicone, epoxy-modified silicone, alkyl-modified silicone, alkoxy-modified silicone, and fatty acid-modified silicone), cyclic dimethylpolysiloxane, and methyl phenyl polysiloxane, and dimethylpolysiloxane, polyether-modified silicone, and amino-modified silicone are preferable. In addition, as these silicones, those diluted with or dispersed in a volatile silicone, a non-volatile silicone or the like, or those dispersed in water may be used.

More specifically, for example, BY11-026, BY22-19, FZ-3125, SH200-1,000,000 cs (Dow Corning Toray Co., Ltd.), TSF451-100MA (Momentive Performance Materials Worldwide LLC) <polysiloxanes>; TSF4440 (Momentive Performance Materials Worldwide LLC), KF-6005, KF-6011 (Shin-Etsu Chemical Co., Ltd.) (polyether-modified silicones]; SF8451C, SF8452C, SF8457C, SM8704C (Dow Corning Toray Co., Ltd.), KF-867 (Shin-Etsu Chemical Co., Ltd.), and SM8904 (Dow Corning Toray Co., Ltd.) <amino-modified silicone> may be included.

These silicones may be used alone or in combination of two or more, and the content of the silicones in the liquid hair dye composition is preferably 0.01% by mass or more, more preferably 0.03% by mass or more, and further more preferably 0.05% by mass or more, and preferably 20% by mass or less, more preferably 15% by mass or less, and further more preferably 5% by mass or less.

Higher Alcohol

A higher alcohol has an effect of improving hair touch feel during rinsing, together with an effect of forming a structure with the surfactant to prevent separation of the hair dye composition. The higher alcohol has preferably 8 to 22 carbon atoms, and more preferably 16 to 22 carbon atoms. Specifically, for example, cetyl alcohol, stearyl alcohol, behenyl alcohol, and the mixtures thereof may be included.

The higher alcohol may be used alone or in combination of two or more, and the content of the higher alcohol in the liquid hair dye composition is preferably 0.01% by mass or more, more preferably 0.1% by mass or more, and preferably 20% by mass or less, more preferably 10% by mass or less.

Organic Conditioning Oil

It is also preferable that the hair dye composition of the present invention contain an organic conditioning oil, for imparting excellent hair touch feel during use. The organic conditioning oil to be preferably used as a conditioning component is preferably a low-viscosity, water-insoluble liquid, and the viscosity of the organic conditioning oil is preferably 1mPa·s or more, more preferably 1 mPa·s or more, and further more preferably 2 mPa·s or more, and, preferably 200 mPa·s or less, more preferably 100 mPa·s or less, and further more preferably 50 mPa·s or less, as measured at 40° C.

The organic conditioning oil may include a hydrocarbon oil, fatty acid ester and the mixtures thereof, and the content thereof is preferably 0.01% by mass or more, more preferably 0.1% by mass or more, and preferably 20% by mass or less, more preferably 10% by mass or less.

Hydrocarbon Oil

The hydrocarbon oil may include, for example, a cyclic hydrocarbon or a saturated or unsaturated straight chain aliphatic hydrocarbon, or saturated or unsaturated branched chain aliphatic hydrocarbon, and the polymers and mixtures thereof. The straight chain hydrocarbon oil has preferably 12 to 19 carbon atoms. The branched chain hydrocarbon oil includes a hydrocarbon polymer, has preferably more than 19 carbon atoms, and includes polyolefins which are a synthetic hydrocarbon oil. The polyolefin is a polyolefin which is a liquid at room temperature, further more preferably liquid poly-α-olefin, and most preferably liquid hydrogenated poly-α-olefin. The polyolefin to be used herein is prepared by polymerizing olefin monomers having 4 to 14 carbon atoms, and preferably 6 to 12 carbon atoms.

Fatty Acid Ester

The fatty acid ester may include, for example, fatty acid esters having at least 10 carbon atoms. The example of these fatty acid esters may include esters having a hydrocarbon chain derived from fatty acid and alcohol (e.g., monoester, polyhydric alcohol ester, and di- and tri-carbonic acid ester). The hydrocarbon group of these fatty acid esters may have other compatible functional group such as an amido group or alkoxy group as a substituent group, or may be covalent-bonded to the groups. More specifically, the alkyl and alkenyl ester of fatty acid having an aliphatic chain having 10 to 22 carbon atoms, aliphatic alcohol/carbonic acid ester having an aliphatic chain derived from alkyl and/or alkenyl alcohol having 10 to 22 carbon atoms, and the mixtures thereof are preferably used.

The specific example of the preferable fatty acid ester may include isopropyl isostearate, hexyl laurate, isohexyl laurate, isohexyl palmitate, isopropyl palmitate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate, and dioleyl adipate.

(Medium)

The first to third agents used in step (I) of the present invention may contain water and/or an organic solvent as a medium. The organic solvent may include lower alkanols such as ethanol, 1-propanol and 2-propanol; aromatic alcohols such as benzyl alcohol and 2-benzyloxyethanol; diols such as propylene glycol, 1,3-butanediol, polyethylene glycol, diethylene glycol; polyols such as glycerin; alkoxy alcohols such as ethoxyethanol, ethoxy diglycol and methoxy ethanol; N-alkylpyrrolidone such as N-methylpyrrolidone and N-ethylpyrrolidone; alkylene carbonates such as propylene carbonate, lactones such as y-valerolactone and y-caprolactone.

These media may be used alone or in combination of two or more. The content of the medium in the mixed solution is preferably 0.05% by mass or more, more preferably 0.1% by mass or more, and further more preferably 0.5% by mass or more, and preferably 30% by mass or less, more preferably 20% by mass or less, and further more preferably 10% by mass or less.

(Other Optional Components)

To the first to third agents used in step (I) of the present invention, other components which are generally used as a cosmetic raw material may be further added, as long as the components do not deteriorate the stable liquid form and the function as the hair dye agent. The optional component may include for example, a penetration enhancer, a pearlizing agent, a preservative, a metal sequestering agent, a stabilizer, an anti-oxidant, a UV absorber, a humectant, or a perfuming agent, and the specific optional component may include for example, higher aliphatic acids, protein hydrolysates, protein derivatives, amino acids, plant extracts, vitamins, or perfumes.

(Dosage Form)

The dosage form of the first and second agents to be used in the present invention may be in a form of for example, liquid, gel, sherbet, slurry, emulsion, cream, ointment, solid paste, or paste, or in a form of aerosol.

The dosage form of the third agent may be in any form of liquid, gel, sherbet, slurry, emulsion, cream, ointment, solid paste, paste, solid, or powder, or may be an aerosol formulation pressing them with gas pressure. From the viewpoint of miscibility, the liquid, emulsion, gel, slurry, cream, paste and powder forms are preferable in order, that is, a liquid formulation is more preferable. In addition, from the viewpoint of dye concentration, the powder, paste, slurry, cream, gel, emulsion, and liquid forms are preferable in order.

When the third agent is prepared in a form of liquid, it is preferable to contain a solvent, from the viewpoint of storage stability. Specifically, it is preferable to contain one or more selected from the group consisting of the lower alkanol, aromatic alcohol, alkoxy alcohol and diol, and the diol is more preferable. When the third agent is prepared in a form of powder, it is preferable to contain a carrier in a form of powder, from the viewpoint of handling. Specifically, silica (silicon dioxide), diatomite, kaolin, bentonite, corn starch, tapioca starch, rice starch, wheat starch, potato starch, nylon powder, montmorillonite, gypsum, sawdust, or pearlite may be included, and among them, cornstarch, diatomite, and silica are preferable.

In addition, it is preferable to mix the first to third agents such that the mixed solution has a viscosity at which the liquid hardly drips down when applied on hair. Specifically, it is preferable that the viscosity of the mixed solution be 2,000 to 100,000 mPa·s, as measured at 30° C. using a B type viscometer (Toki Sangyo Co., Ltd., TVB-10 type) equipped with a helical stand (T-Bar Stage TS-20).

(pH)

The pH of the mixed solution is preferably 7.5 or more, more preferably 8.0 or more, further more preferably 8.5 or more, and further more preferably 9.0 or more, from the viewpoint of obtaining a sufficient hair dyeability, and preferably 12.0 or less, more preferably 11.5 or less, further more preferably 11.0 or less, from the viewpoint of suppressing skin irritation. In addition, it is preferable that the pH of the first agent be 8 or more and 12 or less, and the pH of the second agent be 2 or more and 5 or less. Furthermore, the pH of the third agent is 7.5 or more and 12 or less, and from the viewpoint of miscibility when mixed with the first agent and the second agent, preferably 8.0 or more, more preferably 8.5 or more, and further more preferably 9.0 or more, and preferably 11.5 or less, more preferably 11.0 or less. In the present invention, the pH of the first to third agents and the mixed solution thereof refers to the value at 25° C. when diluted at 10 times by mass with water.

The pH adjusting agent for adjusting the pH of the composition to the above pH may include inorganic acids such as hydrochloric acid and phosphoric acid, organic acids such as citric acid, glycolic acid and lactic acid, hydrochlorides such as ammonium chloride and hydrochloric acid monoethanolamine, and phosphates such as potassium dihydrogen phosphate, disodium hydrogen phosphate, in addition to the alkaline agent.

(Step (I))

Step (I) of the present invention is a step of mixing the first agent containing the alkaline agent and the oxidation dye precursor, the second agent containing the oxidizing agent, and the third agent containing one or more dyes (A) selected from the group consisting of (A-1), (A-2), and (A-3).

The content of the alkaline agent in the mixed solution prepared in step (I) is preferably 0.05% by mass or more, more preferably 0.1% by mass or more, further more preferably 0.2% by mass or more, and further more preferably 0.4% by mass or more, and preferably 7% by mass or less, more preferably 6% by mass or less, and further more preferably 4% by mass or less, from the viewpoint of sufficiently swelling hair to obtain a hair dyeability.

The content of the precursor in the mixed solution is preferably 0.001% by mass or more, more preferably 0.002% by mass or more, further more preferably 0.004% by mass or more, further more preferably 0.01% by mass or more, and preferably 8% by mass or less, more preferably 6% by mass or less, further more preferably 4% by mass or less, and further more preferably 2% by mass or less, from the viewpoint of obtaining a sufficient hair dyeability. In addition, from the same viewpoint, the content of the coupler in the mixed solution is preferably 0.001% by mass or more, more preferably 0.002% by mass or more, further more preferably 0.004% by mass or more, and further more preferably 0.01% by mass or more, and preferably 8% by mass or less, more preferably 6% by mass or less, further more preferably 4% by mass or less, and further more preferably 2% by mass or less.

The content of the oxidizing agent in the mixed solution is preferably 0.06% by mass or more, more preferably 0.1% by mass or more, further more preferably 0.2% by mass or more, further more preferably 0.5% by mass or more, and further more preferably 1% by mass or more, and preferably 17% by mass or less, more preferably 12.5% by mass or less, further more preferably 11% by mass or less, and further more preferably 9% by mass or less, from the viewpoint of hair bleachability and a hair dyeability.

The content of dye (A) in the mixed solution is preferably 0.02% by mass or more, more preferably 0.05% by mass or more, further more preferably 0.08% by mass or more, and further more preferably 0.10% by mass or more, from the viewpoint of obtaining a hair dyeability to dye hair in two layers of colors to change the hue or color tone of hair appearance depending on the viewing angle to the hair, and preferably 5% by mass or less, more preferably 2% by mass or less, further more preferably 1.0% by mass or less, and further more preferably 0.5% by mass or less, from the viewpoint of being dissolved in the mixed solution to obtain uniform dyeing.

In step (I), from the viewpoint of dye hair in two layers, and change the hue or color tone of hair appearance depending on the viewing angle to the hair, the mass ratio of dye (A) and the precursor (dye (A)/precursor) in the mixed solution is preferably 0.005 or more, more preferably 0.015 or more, further more preferably 0.03 or more, further more preferably 0.1 or more, further more preferably 0.2 or more, and further more preferably 0.3 or more, and, preferably 5,000 or less, more preferably 500 or less, further more preferably 100 or less, further more preferably 50 or less, further more preferably 10 or less, and further more preferably 8 or less.

(Mixing Ratio)

The mixing mass ratio of the first agent and the second agent (second agent/first agent) is preferably 0.2 to 5, more preferably 0.3 to 3, and further more preferably 0.5 to 2, from the viewpoint of obtaining a sufficient hair dyeability. In addition, a ratio of the mass of the third agent with respect to the total mass of the first agent and the second agent (third agent/(first agent+second agent)) is preferably from 0.01 to 0.4, more preferably 0.02 to 0.3, and further more preferably from 0.03 to 0.2, from the viewpoint of dyeing hair in two layers of colors to have a high dyeing effect of changing the hue or color tone of hair appearance depending on the viewing angle to the hair.

(Step (II))

Step (II) is a step of applying the mixed solution prepared in step (I) on hair. When the mixed solution is applied on hair, a bath ratio, that is, a ratio of the mass of the applied mixed solution with respect to the mass of hair, (mass of the applied mixed solution)/(mass of hair), a standing time from applying the mixed solution on hair to washing hair, and a standing temperature have a great influence on finishing.

The bath ratio, (mass of the applied mixed solution)/(mass of hair) is preferably 0.2 or more, more preferably 0.4 or more, and further more preferably 0.6 or more, from the viewpoint of improving a hair dyeability and preventing color unevenness, and preferably 2 or less, more preferably 1.75 or less, further more preferably 1.5 or less, from the viewpoint of economic feasibility and reducing a risk of dripping.

The standing time from applying the mixed solution on hair to washing hair is preferably 1 minute or more, more preferably 5 minutes or more, further more preferably 10 minutes or more, from the viewpoint of improving a hair dyeability, and preferably 60 minutes or less, more preferably 45 minutes or less, and further more preferably 40 minutes or less, from the viewpoint of suppressing skin irritation.

The temperature during applying the mixed solution on hair and allowing the mixed solution to stand is preferably 5° C. or more, more preferably 10° C. or more, and further more preferably 20° C. or more, from the viewpoint of improving a hair dyeability, and preferably 60° C. or less, more preferably 50° C. or less, and further more preferably 40° C. or less, from the viewpoint of suppressing skin irritation.

(Step (III))

After step (II), the hair may be rinsed and/or washed. For rinsing, an optional aqueous medium which is known in the art, preferably water, more preferably tap water may be used, and for washing, an optional cleansing composition which is known in the art, preferably a shampoo composition may be used. The root part, the distal end part and the part therebetween of hair may be rinsed and/or washed at the same time or separately.

(Step (IV))

After step (III), or before step (III), or instead of step (III), an optional conditioning composition which is known in the art may be applied to hair.

(Step (V))

Hair may be dried after step (II), (III), or (IV). For drying hair, a drying tool, for example towel, or an electric drying tool such as a hair dryer may be used, and drying may be performed partially or completely.

Hereinafter, for the embodiments as described above, the preferable embodiment of the present invention is further disclosed.

<1> Hair dyeing method comprising the following steps (I) and (II):

step (I): mixing a first agent comprising an alkaline agent and an oxidation dye precursor, a second agent comprising an oxidizing agent, and a third agent comprising one or more dyes (A) selected from the group consisting of the following (A-1), (A-2), and (A-3), having a pH at 25° C. of 7.5 or more and 12 or less when diluted to be 10 times by mass with water, so that the content of dye (A) in a mixed solution is from 0.05 to 2% by mass; and step (II): applying the mixed solution prepared in step (I) on hair:

[Chem. 3]

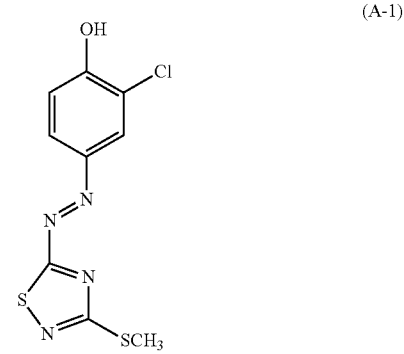

(A-1)

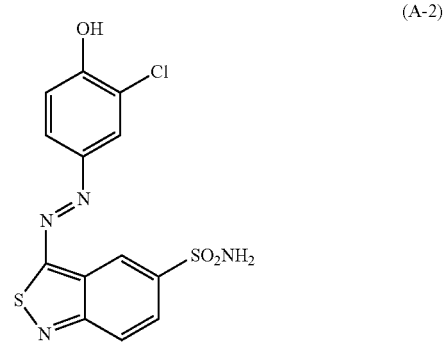

(A-2)

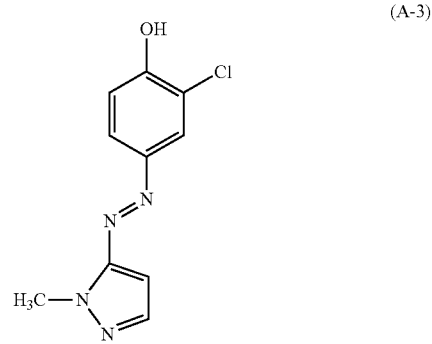

(A-3)

<2> Hair dyeing method comprising the following steps (I) and (II):

step (I): mixing a first agent comprising an alkaline agent and an oxidation dye precursor, a second agent comprising an oxidizing agent, and a third agent comprising one or more dyes (A) selected from the group consisting of the following (A-1), (A-2), and (A-3), having a pH at 25° C. of 7.5 or more and 12 or less when diluted to be 10 times by mass with water, so that a mass ratio of dye (A) and the precursor (dye (A)/precursor) in a mixed solution is from 0.2 to 10; and step (II): applying the mixed solution prepared in step (I) on hair:

[Chem. 4]

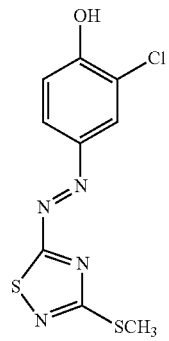
(A-1)

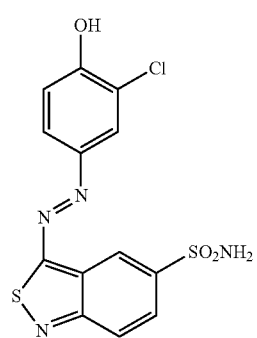
(A-2)

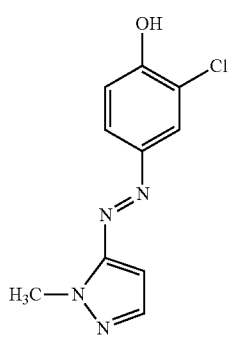
(A-3)

<3> Hair dyeing method comprising the following steps (I) and (II):

step (I): mixing a first agent comprising an alkaline agent and an oxidation dye precursor, a second agent comprising an oxidizing agent, and a third agent comprising one or more dyes (A) selected from the group consisting of the following (A-1), (A-2), and (A-3), having a pH at 25° C. of 7.5 or more and 12 or less when diluted to be 10 times by mass with water, so that a ratio of the mass of the third agent with respect to the total mass of the first agent and the second agent (third agent/(first agent+second agent)) is in a range of from 0.01 to 0.4; and step (II): applying the mixed solution prepared in step (I) on hair:

[Chem. 5]

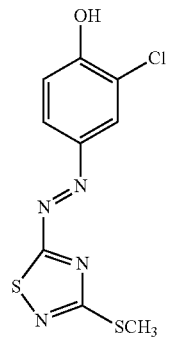
(A-1)

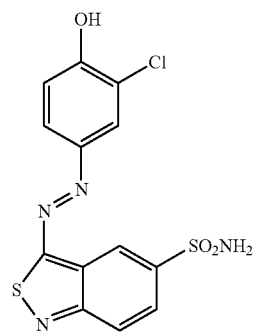
(A-2)

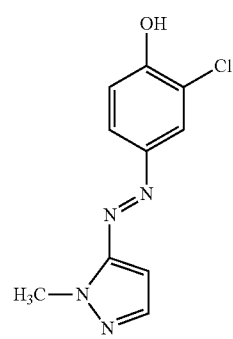
(A-3)

<4> Hair dyeing method comprising the following steps (I) and (II):

step (I): mixing a first agent comprising an alkaline agent and an oxidation dye precursor, a second agent comprising an oxidizing agent, and a third agent comprising one or more dyes (A) selected from the group consisting of the following (A-1), (A-2), and (A-3), having a pH at 25° C. of 7.5 or more and 12 or less when diluted to be 10 times by mass with water, so that the content of dye (A) in a mixed solution is from 0.08 to 1% by mass and a mass ratio of dye (A) and the precursor (dye(A)/precursor) in the mixed solution is from 0.2 to 8; and step (II): applying the mixed solution prepared in step (I) on hair:

[Chem. 6]

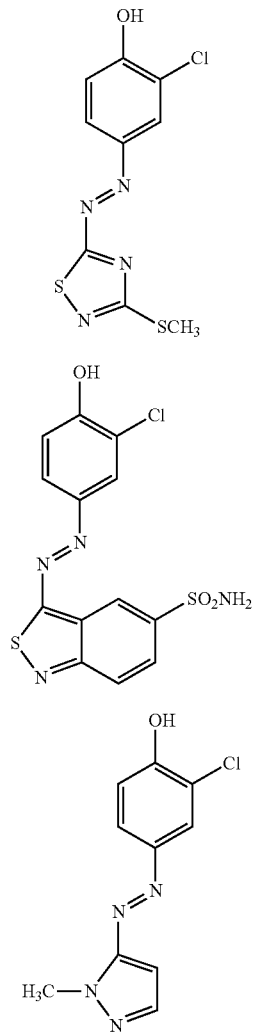

<5> The hair dyeing method according to any one of <1> to <3>, where in step (I), the mixing is carried out, so that the mass ratio of dye (A) and the precursor in the mixed solution (dye (A)/precursor) is from 0.2 to 8.

<6> The hair dyeing method according to any one of <1> to <3>, where in step (I), the mixing is carried out, so that the content of dye (A) is from 0.08 to 1.0% by mass.

<7> The hair dyeing method according to any one of <1>, <2>, and <4> to <6>, where in step (I), the mixing is carried out, so that a ratio of the mass of the third agent with respect to the total mass of the first agent and the second agent (third agent/(first agent+second agent)) is in a range of from 0.01 to 0.4.

<8> The hair dyeing method according to any one of <1> to <7>, where the third agent comprises one or more alkanol amines as the alkaline agent.

<9> The hair dyeing method according to any one of <1> to <8>, where the third agent is in a form of liquid, powder, or slurry.

<10> The hair dyeing method according to any one of <1> to <8>, where the third agent is in a form of liquid.

<11> The hair dyeing method according to any one of <1> to <10>, where the third agent has a pH of 8.5 or more and 11 or less at 25° C. when diluted to be 10 times by mass with water.

<12> A third agent composition for hair dyeing, used by mixing the composition with a first agent comprising an alkaline agent and an oxidation dye precursor, and a second agent comprising an oxidizing agent, the composition comprising 0.5 to 20% by mass of one or more dyes (A) selected from the group consisting of the following (A-1), (A-2), and (A-3), having a pH at 25° C. of 7.5 or more and 12 or less when diluted to be 10 times by mass with water:

[Chem. 7]

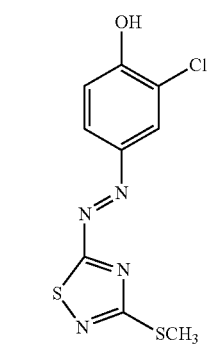

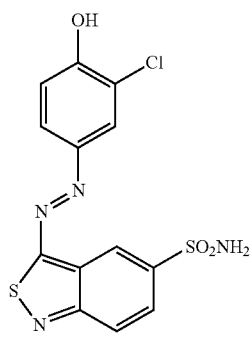

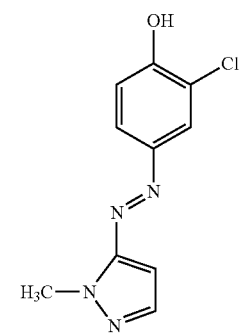

<13> The third agent composition for hair dyeing according to <12>, where one or more alkanolamine are included as the alkaline agent.

<14> The third agent composition according to <12> or <13>, where the composition is in a form of liquid, powder, or slurry.

<15> The third agent composition according to <12> or <13>, where the composition is in a form of liquid.

<16> The third agent composition according to any one of <12> to <15>, where one or more selected from the group consisting of lower alkanol, aromatic alcohol, alkoxy alcohol and diol, preferably diol is included as a solvent.

EXAMPLES (Preparation of hair cosmetics)

Examples 1 to 14 and Comparative Examples 1 to 4

Each component shown in Tables 1 to 3 was mixed to prepare the first agent, the second agent, and the third agent, respectively, which were stored at 50° C. for two months, and the following evaluation was performed. In addition, the pH of the third agent was measured by uniformly mixing 10 g of the third agent and 90 g of ion exchange water to prepare an aqueous solution of 10% by mass, and using a benchtop pH meter (F-72) manufactured by Horiba, Ltd.

<Hair Dyeing Method>

White hair purchased from IHIP was used to manufacture a hair tress having a length of 15 cm and a weight of about 1 g, which was hair for evaluation. 4 g of the first agent, 6 g of the second agent, and 1.25 g of the third agent were weighed into a plastic beaker, and mixed with a spatula until uniform. About 1 g of this mixed solution was applied on the hair for evaluation with a brush, and allowed to stand at 30° C. for 30 minutes to dye the hair. The hair was rinsed with warm water at 40° C. for 30 seconds or more, and cleaned with shampoo, treated with a conditioner, and dried.

(Evaluation Method of Miscibility of Composition)

From the time required for uniformly mixing the first to third agents by stirring the agents with a spatula, miscibility was evaluated by the following five steps:
1: uniformly mixed in 10 seconds or less;
2: uniformly mixed in 11 to 30 seconds;
3: uniformly mixed in 31 seconds to 1 minute;
4: uniformly mixed in 1 to 2 minutes; and
5: uniformly mixed in 2 minutes or more.

(Evaluation Method of Change of Hue or Color Tone of Hair Appearance Depending on Viewing Angle to the Hair)

Dried hair after being dyed was observed under an artificial sun light (Format XC-100AP, 100W)) manufactured by Seric Co. Ltd., from a distance of about 30 cm as a hair tress. An evaluator fixed one end of the hair tress for evaluation, and moved the other end to change the angle to the hair, thereby observing the change of hair color. The evaluation was performed by five evaluators, by evaluating a degree of color change in a non-restrictive selection answer manner of a direct determination method. That is, a straight line of 10 cm in length was drawn horizontally, where the left end of the straight line was "color change was not felt even with the change of angle", and the right end of the straight line was "different colors are seen depending on angle", and the evaluation was shown by checking how many centimeters from the left end on the straight line the hairs of the Examples and the Comparative Examples were positioned. The average from the five evaluators is shown in Tables 1 to 3 as scores.

TABLE 1

| | | | Example | | | | | | Comparative Example | |
|---|---|---|---|---|---|---|---|---|---|---|
| | | | 1 | 2 | 3 | 4 | 5 | 6 | 1 | 2 |
| Composition of each agent (% by mass) | First agent | Toluene-2,5-diamine | 0.380 | 0.380 | 0.380 | 0.380 | 0.380 | 0.380 | 0.380 | 0.380 |
| | | 2,4-Diaminophenoxyethanol hydrochloride | 0.525 | 0.525 | 0.525 | 0.525 | 0.525 | 0.525 | 0.525 | 0.525 |
| | | Dye (A-1); HC Red 18 | — | — | — | — | — | — | — | 0.825 |
| | | Ascorbic acid | 0.15 | 0.15 | 0.15 | 0.15 | 0.15 | 0.15 | 0.15 | 0.15 |
| | | Anhydrous sodium sulfite | 0.20 | 0.20 | 0.20 | 0.20 | 0.20 | 0.20 | 0.20 | 0.20 |
| | | Ammonia water (28% by mass) | 6.00 | 6.00 | 6.00 | 6.00 | 6.00 | 6.00 | 6.00 | 6.00 |
| | | EDTA•4Na | 0.05 | 0.05 | 0.05 | 0.05 | 0.05 | 0.05 | 0.05 | 0.05 |
| | | Purified water | 92.695 | 92.695 | 92.695 | 92.695 | 92.695 | 92.695 | 92.695 | 91.870 |
| | | Sum of first agent | 100.0 | 100.0 | 100.0 | 100.0 | 100.0 | 100.0 | 100.0 | 100.0 |
| | Second agent | Hydrogen peroxide (35% by mass) | 5.8 | 5.8 | 5.8 | 5.8 | 5.8 | 5.8 | 5.8 | 5.8 |
| | | Purified water | 94.2 | 94.2 | 94.2 | 94.2 | 94.2 | 94.2 | 94.2 | 94.2 |
| | | Sum of second agent | 100.0 | 100.0 | 100.0 | 100.0 | 100.0 | 100.0 | 100.0 | 100.0 |
| | Third agent | Dye (A-1); HC Red 18 | 3.00 | 0.52 | 0.73 | 1.16 | 4.50 | 6.04 | — | — |
| | | Acid Red 33 (Red 227) | — | — | — | — | — | — | 3.00 | — |
| | | 2-Amino-2-methyl propanol | 4.00 | 4.00 | 4.00 | 4.00 | 4.00 | 4.00 | 4.00 | 4.00 |
| | | Propylene glycol | 25.00 | 25.00 | 25.00 | 25.00 | 25.00 | 25.00 | 25.00 | 25.00 |
| | | EDTA•4Na | — | 0.05 | 0.05 | 0.05 | 0.05 | 0.05 | — | 0.05 |
| | | Purified water | 68.00 | 70.43 | 70.22 | 69.79 | 66.45 | 64.91 | 68.00 | 70.95 |
| | | Sum of third agent | 100.0 | 100.0 | 100.0 | 100.0 | 100.0 | 100.0 | 100.0 | 100.0 |
| | | pH (25° C., 10% by mass aqueous solution) | 10.16 | 10.93 | 10.72 | 10.57 | 10.08 | 9.90 | 11.24 | 11.17 |
| Mixed solution | | Content of precursor (% by mass) | 0.135 | 0.135 | 0.135 | 0.135 | 0.135 | 0.135 | 0.135 | 0.135 |
| | | Content of direct dye (% by mass) | 0.333 | 0.058 | 0.082 | 0.129 | 0.500 | 0.671 | 0.333 | 0.293 |
| | | Direct dye/precursor (mass ratio) | 2.467 | 0.428 | 0.604 | 0.955 | 3.701 | 4.967 | 2.467 | 2.171 |
| Evaluation | | Miscibility | 1 | 1 | 1 | 1 | 1 | 1 | 1 | 1 |
| | | Change of hue or color tone depending on viewing angle to the hair | 6.8 | 3.3 | 4.2 | 5.5 | 5.2 | 4.9 | 2.0 | 2.9 |

TABLE 2

|  |  | (% by mass) | Example 7 | Example 8 | Example 9 | Example 10 |
|---|---|---|---|---|---|---|
| Composition of each agent (% by mass) | First agent | Toluene-2,5-diamine | 1.818 | 0.005 | 0.023 | 2.300 |
|  |  | 2,4-Diaminophenoxyethanol hydrochloride | 2.512 | 0.006 | 0.032 | 3.178 |
|  |  | Ascorbic acid | 0.15 | 0.15 | 0.15 | 0.15 |
|  |  | Anhydrous sodium sulfite | 0.20 | 0.20 | 0.20 | 0.20 |
|  |  | Ammonia water (28% by mass) | 6.00 | 6.00 | 6.00 | 6.00 |
|  |  | EDTA·4Na | 0.05 | 0.05 | 0.05 | 0.05 |
|  |  | Purified water | 89.270 | 93.589 | 93.545 | 88.122 |
|  |  | Sum of first agent | 100.0 | 100.0 | 100.0 | 100.0 |
|  | Second agent | Hydrogen peroxide (35% by mass) | 5.8 | 5.8 | 5.8 | 5.8 |
|  |  | Purified water | 94.2 | 94.2 | 94.2 | 94.2 |
|  |  | Sum of second agent | 100.0 | 100.0 | 100.0 | 100.0 |
|  | Third agent | Dye (A-1); HC Red 18 | 1.16 | 0.73 | 0.73 | 0.73 |
|  |  | 2-Amino-2-methyl propanol | 4.00 | 4.00 | 4.00 | 4.00 |
|  |  | Propylene glycol | 25.00 | 25.00 | 25.00 | 25.00 |
|  |  | EDTA·4Na | 0.05 | 0.05 | 0.05 | 0.05 |
|  |  | Purified water | 69.79 | 70.22 | 70.22 | 70.22 |
|  |  | Sum of third agent | 100.0 | 100.0 | 100.0 | 100.0 |
|  |  | pH (25° C., 10% by mass aqueous solution) | 10.57 | 10.72 | 10.72 | 10.72 |
| Mixed solution | | Content of precursor (% by mass) | 0.646 | 0.002 | 0.008 | 0.818 |
|  |  | Content of direct dye (% by mass) | 0.129 | 0.082 | 0.082 | 0.082 |
|  |  | Direct dye/precursor (mass ratio) | 0.200 | 49.891 | 9.978 | 0.100 |
| Evaluation | | Miscibility | 1 | 1 | 1 | 1 |
|  |  | Change of hue or color tone depending on viewing angle to the hair | 3.9 | 3.0 | 3.5 | 3.7 |

TABLE 3

|  |  | (% by mass) | Example 11 | Example 12 | Example 13 | Example 14 | Comparative Example 3 | Comparative Example 4 |
|---|---|---|---|---|---|---|---|---|
| Composition of each agent (% by mass) | First agent | Toluene-2,5-diamine | 0.150 | — | 0.380 | 0.380 | 0.380 | 0.380 |
|  |  | 2,4-diaminophenoxyethanol hydrochloride | 0.260 | — | 0.525 | 0.525 | 0.525 | 0.525 |
|  |  | p-aminophenol | — | 0.898 | — | — | — | — |
|  |  | Resorcin | — | 0.880 | — | — | — | — |
|  |  | 5-Amino-o-cresol | — | 0.010 | — | — | — | — |
|  |  | Ascorbic acid | 0.15 | 0.15 | 0.15 | 0.15 | 0.15 | 0.15 |
|  |  | Anhydrous sodium sulfite | 0.20 | 0.20 | 0.20 | 0.20 | 0.20 | 0.20 |
|  |  | Ammonia water (28% by mass) | 6.00 | 6.00 | 6.00 | 6.00 | 6.00 | 6.00 |
|  |  | EDTA·4Na | 0.05 | 0.05 | 0.05 | 0.05 | 0.05 | 0.05 |
|  |  | Purified water | 93.190 | 91.812 | 92.695 | 92.695 | 92.695 | 92.695 |
|  |  | Sum of first agent | 100.0 | 100.0 | 100.0 | 100.0 | 100.0 | 100.0 |
|  | Second agent | Hydrogen peroxide (35% by mass) | 5.8 | 5.8 | 5.8 | 5.8 | 5.8 | 5.8 |
|  |  | Purified water | 94.2 | 94.2 | 94.2 | 94.2 | 94.2 | 94.2 |
|  |  | Sum of second agent | 100.0 | 100.0 | 100.0 | 100.0 | 100.0 | 100.0 |
|  | Third agent | Dye (A-1); HC Red 18 | — | — | 3.00 | 3.00 | 3.00 | 10.00 |
|  |  | Dye (A-2); HC Blue 18 | — | 3.00 | — | — | — | — |
|  |  | Dye (A-3); HC Yellow 16 | 3.00 | — | — | — | — | — |
|  |  | 2-Amino-2-methyl propanol | 4.00 | 4.00 | 4.00 | 4.00 | — | — |
|  |  | Propylene glycol | 25.00 | 25.00 | 25.00 | 25.00 | — | — |
|  |  | EDTA·4Na | 0.05 | 0.05 | 0.05 | 0.05 | — | — |
|  |  | Liquid paraffin*1 | — | — | — | — | 97.00 | 90.00 |
|  |  | Phosphoric acid (75%) | — | — | 2.00 | 3.00 | — | — |
|  |  | Purified water | 67.95 | 67.95 | 65.95 | 64.95 | 0.00 | 0.00 |
|  |  | Sum of third agent | 100.0 | 100.0 | 100.0 | 100.0 | 100.0 | 100.0 |
|  |  | pH (25° C., 10% by mass aqueous solution) | 10.54 | 10.19 | 8.55 | 7.77 | 6.27 | 5.80 |
|  |  | Content of precursor (oxidation dye precursor) (% by mass) | 0.053 | 0.319 | 0.135 | 0.135 | 0.135 | 0.135 |
| Mixed solution | | Content of direct dye (% by mass) | 0.333 | 0.333 | 0.333 | 0.333 | 0.333 | 1.111 |
|  |  | Direct dye/precursor (mass ratio) | 6.250 | 1.044 | 2.467 | 2.467 | 2.467 | 8.224 |
| Evaluation | | Miscibility | 1 | 1 | 1 | 1 | 5 | 5 |
|  |  | Change of hue or color tone defending on viewing angle to the hair | 8.1 | 6.4 | 6.1 | 6.2 | 4.8 | 3.8 |

*1HICALL K-350 (manufactured by Kaneda Co., Ltd.)

The invention claimed is:

1. A hair dyeing method, comprising:

(I): mixing a first agent comprising an alkaline agent and an oxidation dye precursor, a second agent comprising an oxidizing agent, and a third agent comprising at least one dye (A) selected from the group consisting of the following (A-1), (A-2), and (A-3), and having a pH at 25° C. of 7.5 or more and 12 or less when diluted to be 10 times by mass with water, to prepare a mixed solution; and (II): applying the mixed solution on hair:

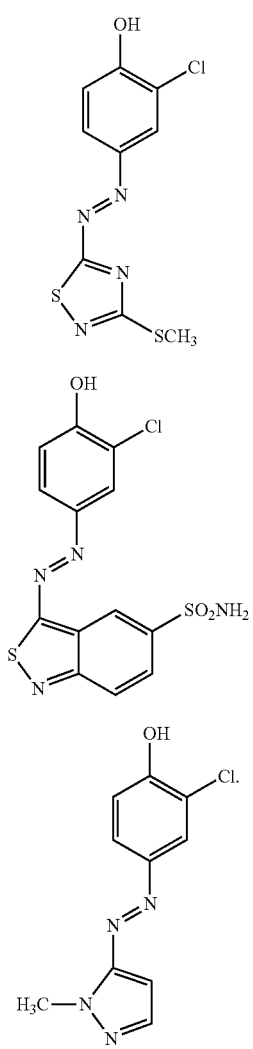

2. The hair dyeing method according to claim 1, wherein in (I), the first agent, the second agent and the third agent are mixed such that a content of the dye (A) in the mixed solution is 0.02% by mass or more.

3. The hair dyeing method according to claim 1, wherein the third agent is in a form of liquid.

4. The hair dyeing method according to claim 1, wherein in (I), the mixing is performed such that a ratio of a mass of the third agent with respect to a total mass of the first agent and the second agent is from 0.01 to 0.4.

5. A third agent composition in a form of a liquid for hair dyeing, comprising:
at least one dye (A) selected from the group consisting of the following (A-1), (A-2), and (A-3), and having a pH of 7.5 or more and 12 or less at 25° C. when diluted to be 10 times by mass with water:

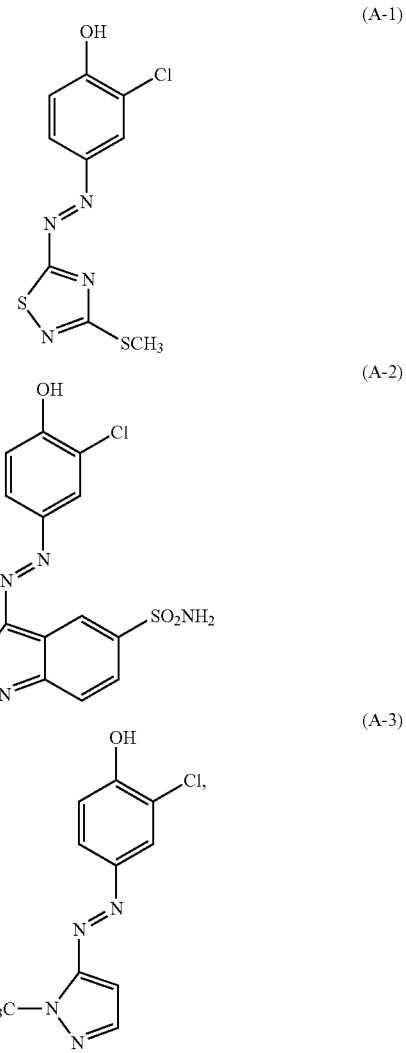

wherein the third agent composition is suitable to be mixed with a first agent comprising an alkaline agent and an oxidation dye precursor, and a second agent comprising an oxidizing agent,
wherein said third agent does not contain an oxidation dye precursor or an oxidizing agent.

6. The third agent composition according to claim 5, wherein a content of the dye (A) is 0.2% by mass or more and 50% by mass or less.

7. The hair dyeing method according to claim 1, wherein a content of the alkaline agent in the mixed solution prepared in (I) is 0.05% by mass or more and 7% by mass or less.

8. The hair dyeing method according to claim 1, wherein a content of the precursor in the mixed solution prepared in (I) is 0.001% by mass or more and 8% by mass or less.

9. The hair dyeing method according to claim 1, wherein a content of the oxidizing agent in the mixed solution prepared in (I) is 0.06% by mass or more and 17% by mass or less.

10. The hair dyeing method according to claim 1, wherein the mixing in (1) is performed such that a mass ratio of the dye (A) and the precursor (dye (A)/precursor) in the mixed solution is 0.2 or more and 8 or less.

11. The third agent composition according to claim 5, further comprising at least one member selected from the group consisting of ethanol, 1-propanol, 2-propanol, benzyl alcohol, 2-benzyloxyethanol, ethoxyethanol, ethoxy diglycol, methoxy ethanol, propylene glycol, 1,3-butanediol, polyethylene glycol and diethylene glycol.

12. The third agent composition according to claim 5, which is an aqueous liquid.

* * * * *